United States Patent [19]

Glass, III

[11] Patent Number: 4,689,985
[45] Date of Patent: Sep. 1, 1987

[54] CALIBRATION IMPACT HAMMER

[75] Inventor: Samuel W. Glass, III, Lynchburg, Va.

[73] Assignee: The Babcock & Wilcox Company, New Orleans, La.

[21] Appl. No.: 836,377

[22] Filed: Mar. 5, 1986

[51] Int. Cl.$^4$ ................................................ G01L 1/00
[52] U.S. Cl. .......................................... 73/1 R; 73/12
[58] Field of Search ..................... 73/1 R, 82, 11, 572, 73/12

[56] References Cited

U.S. PATENT DOCUMENTS

| 3,435,658 | 4/1969 | Arthur | 73/12 |
| 3,538,743 | 11/1970 | Glidden | 73/12 |
| 4,399,685 | 8/1983 | Atkey | 73/11 |
| 4,422,320 | 12/1983 | Moorby et al. | 73/12 |

FOREIGN PATENT DOCUMENTS

| 0082028 | 6/1980 | Japan | 73/12 |
| 0005925 | 1/1984 | Japan | 73/572 |
| 0939988 | 6/1982 | U.S.S.R. | 73/12 |

OTHER PUBLICATIONS

Henderson et al., "An Optical System For Measurement of Energy for Pendulum Impact Machines", pp. 35-39, ISA Transactions, vol. 18, No. 3, 1979.

Primary Examiner—Stewart J. Levy
Assistant Examiner—Robert R. Raevis
Attorney, Agent, or Firm—Robert J. Edwards; D. Neil LaHaye

[57] ABSTRACT

An instrumented hammer that gives the operator a measurement of the impact energy of each hammer blow. A head or main body portion slidably receives an inertia rod spring mounted in a longitudinal bore therein. Upon striking a surface, momentum causes movement of the rod forward against the spring pressure. A slot on the rod moves through an optical switch which emits a signal relative to the movement of the slot therethrough. A display assembly receives the signal and calculates the impact energy of the hammer blow.

14 Claims, 7 Drawing Figures

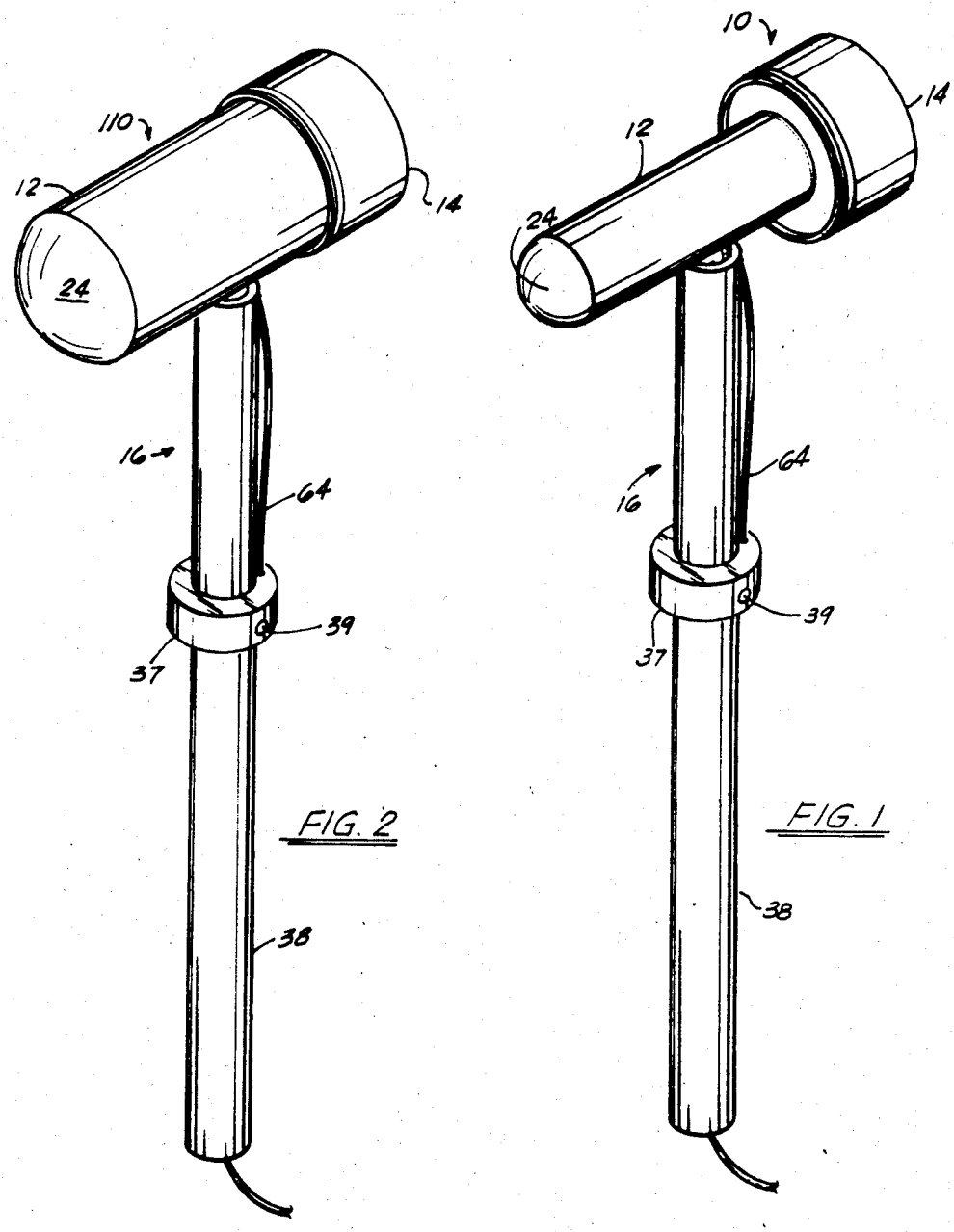

CALIBRATION IMPACT HAMMER

BACKGROUND OF THE INVENTION

1. Field of the Invention

The invention is related to loose parts monitor systems on commercial nuclear power plants and in particular to an impact hammer used to calibrate the time delay and amplitude response characteristics of a loose parts monitor system.

2. General Background

A loose parts monitor system (LPMS) is installed on most commercial nuclear reactors in response to U.S. Nuclear Regulatory Commission Regulatory Guide 1.333. As stated therein and well known in the industry, the presence of a loose part in the primary coolant system may be indicative of degraded reactor safety. A LPMS is required to be capable of detecting a metallic loose part that weighs from 0.25 lbs. (0.11 Kg) to 30 lbs. (13,6 Kg) and impacts with a kinetic energy of 0.5 ft.lb. (0.68 joules) or more on the inside surface of the reactor coolant pressure boundary within three feet (0.91 meter) of a sensor. It is further required that the alert logic of the system have the capability to distinguish the transient signal caused by the impact of a loose part from the normal background signals associated with hydraulic, mechanical, and electrical noise and large-amplitude electrical transients.

As known in the present state of the art, the conventional method for calibrating the LPMS is to impact the outside of the primary pressure boundary with either free falling weights or pendulum weights. The impact energy is determined from the product of the mass of the weight times the height from which it is dropped. This data is then used to calibrate the LPMS time delay and amplitude response characteristics. However, this method of using free falling or pendulum weights can be difficult to control and is often impossible to implement for surfaces where impacting must be in an upward direction.

SUMMARY OF THE INVENTION

The present invention solves the above problem in a straightforward manner. What is provided is an instrumented hammer which is designed in response to regulatory guide 1.133 requirements and gives the operator a measurement of the impact energy of each hammer blow. The hammer includes a main body portion having a longitudinal bore which slidably receives an inertia rod. The inertia rod is biased away from the first or impact end of the hammer by a spring in the longitudinal bore. A groove is provided near one end of the inertia rod. After striking of the first end of the hammer against the reactor surface, the momentum of the rod causes it to continue forward movement against the spring pressure. The groove on the rod activates an optical switch mounted on the second end of the main body portion. The relative velocity between the hammer and the inertia rod is determined by a computer which receives signals from the optical switch and then calculates the impact energy of the blow.

In view of the above, it is an object of the present invention to provide a calibration impact hammer in response to regulatory guide 1.133 calibration requirements.

It is another object of the invention to provide an impact hammer which gives the operator a measurement of the impact energy of each hammer blow.

It is a further object of the invention to provide an impact hammer which makes it possible to calibrate on surfaces at any orientation, including surfaces which must be impacted in an upward direction.

BRIEF DESCRIPTION OF THE DRAWINGS

For a further understanding of the nature and objects of the present invention, reference should be had to the following description, taken in conjunction with the accompanying drawings in which like parts are given like reference numerals and, wherein:

FIG. 1 is a perspective view of one size hammer of the invention.

FIG. 2 is a perspective view of a second size hammer of the invention.

DETAILED DESCRIPTION OF THE PREFERRED EMBODIMENT

Figure 4:
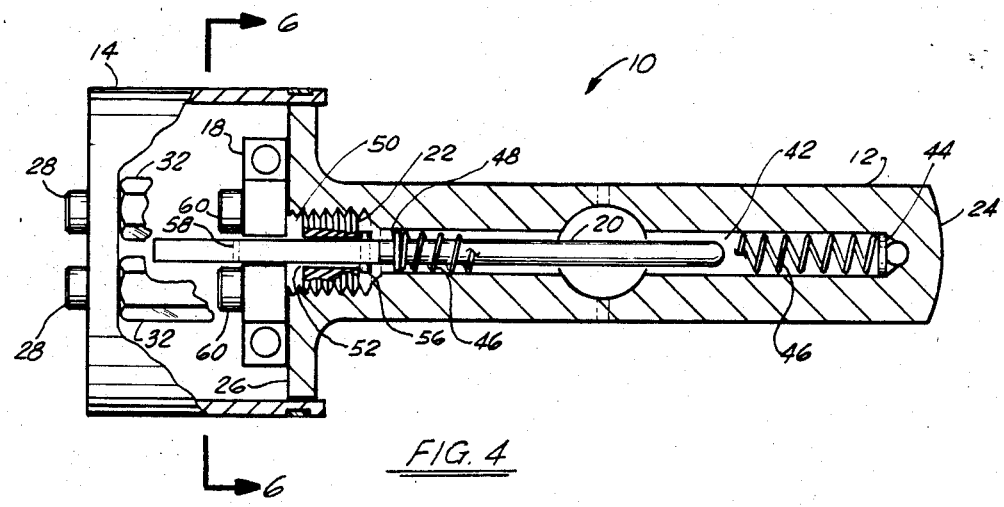
FIG. 4 is a cutaway view illustrating the internal structure of the hammer of FIG. 1.

Referring now to the drawings, it is seen that the invention is generally referred to by the numeral 10. As best seen in FIGS. 1 and 4, hammer 10 is generally comprised of head 12, cover 14, handle 16, optical switch means 18, inertia rod 20, and guide bushing 22.

Although head 12 is illustrated as being circular in cross section, it may be of any suitable shape and is preferably formed from a material of suitable hardness and durability for striking the primary pressure boundary such as 4140 steel having a cadmium plate finish. Use of such a material also provides for tools of varying weights in convenient sizes which may be used in confined spaces. Head 12 is provided with a first or impact end 24 which is preferably convex in shape to insure solid single point contact when striking the pressure boundary. Head 12 is provided with second end 26 which extends radially outward to a diameter greater than the remainder of head 12 and serves as means for attaching cover 14 thereto. Cover 14 is preferably formed from a material which is durable yet lightweight such as delrin so that it comprises a small percentage of the total mass of hammer 10. The weight of handle 16 is not included in determining the dynamic weight of hammer 10 as handle 16 is resiliently isolated from head 12.

Figure 6:
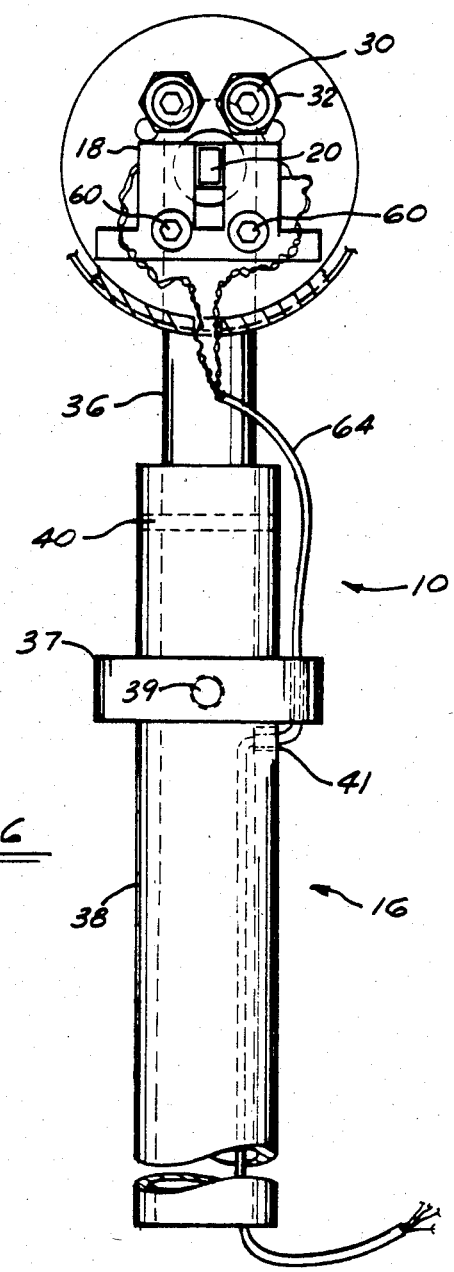
FIG. 6 is a sectional view along lines 6—6 of FIG. 4.

Cover 14 is attached to head 12 at second end 26 by means of screws 28 threaded through cover 14 and threadably engaged in threaded bores 30 in second end 26, best seen in FIG. 6. Spacers 32 are provided to insure proper positioning of cover 14 upon tightening of screws 26.

Handle 16, best seen in FIG. 6, is comprised of elastomeric mounting stem 36 and grip 38. Mounting stem 36 is preferably formed from reinforced rubber having a generally cylindrical shape. Grip 38 is preferably formed from tubular stainless steel having an inner diameter substantially near that of the outer diameter of mounting stem 36 to provide for a close fit. Any suitable means for mounting stem 36 to head 12 and grip 38 such as epoxy cement may be used. To prevent sliding of grip 38 along stem 36 and insure that the preferred clearance of one-half inch between head 12 and grip 38 is maintained, roll pin 40 may be inserted therethrough. A sleeve 37 attached to grip 38 by insert 39 serves as a retainer for wiring harness 64 adjacent grommet 41 is used to feed wiring harness 64 into grip 38.

As best seen in FIG. 4, head 12 is provided with a longitudinal bore 42 for slidably receiving inertia rod 20. Bore 42 is open at second end 26 and closed near first end 24 of head 12. A first stop ring 44 is positioned at the end of bore 42 to provide for proper loading of spring 46 against second stop ring 48 on inertia rod 20. A larger threaded bore 50 is provided at the end of longitudinal bore 42 at end 26 for threadably receiving guide bushing 22. Guide bushing 22 is provided with a central bore 52 to allow sliding of inertia rod 20 therein between a first normal retracted position and a second inserted position. When threadably engaged in bore 50, guide bushing 22 has its central bore 52 in coaxial alignment with longitudinal bore 42 and serves to limit the movement of inertia rod 20 toward second end 26 and provide proper positioning of inertia 20 relative to optical switch means 18.

Figure 5:
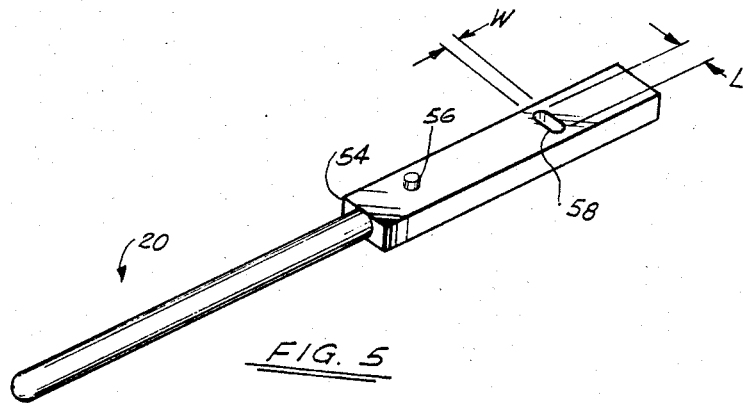
FIG. 5 illustrates the inertia rod of the invention.

As illustrated in FIG. 5, inertia rod 20 has a reduced diameter at its forward end and a rear section which is rectangular in cross section. This forms a raised shoulder portion 54 which serves to prevent movement of second stop ring 48 when positioned within longitudinal bore against the biasing action of spring 46. Inertia rod 20 is also provided with means for adjusting its position in longitudinal bore 42 such as radially extending spring pin 56. Radial spring pin 56 extends outwardly from inertia rod 20 less than the diameter of longitudinal bore 42 to allow movement therein but greater than the diameter of central bore 52 in guide bushing 22. Thus, during assembly of hammer 10, pin 56 bears against guide bushing 22 and the relative positioning of guide bushing 22 is used to adjust the position of inertia rod 20 and slot 58 relative to optical switch means 18. As illustrated in FIGS. 4 and 5, slot 58 extends through rod 20 near its rearward end, is preferably of an oblong shape and lies at approximately a 90° angle to the longitudinal axis of rod 20. Thus, movement of inertia rod 20 in longitudinal bore 42 causes slot 58 to pass through optical switch means 18. This allows passage of light energy emitted by one portion of optical switch means 18 to pass through slot 58 and activate the light sensing or receiving means in optical switch means 18 for the length of time it takes slot 58 to travel therethrough.

Figure 7:
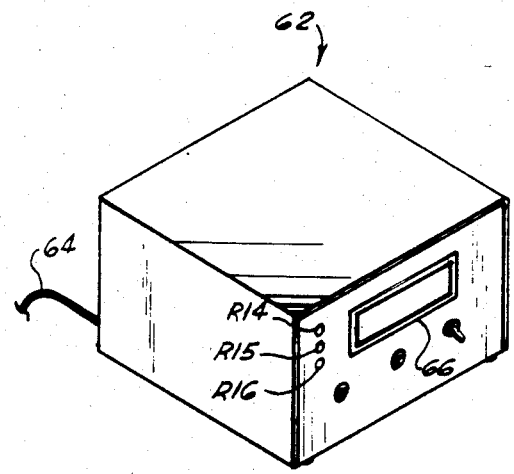
FIG. 7 illustrates the kinetic energy display assembly of the invention.

Optical switch means 18, illustrated in FIGS. 4 and 6, is mounted to head 12 by screws 60 and may be any suitable type known having a light energy emitting section and a light sensing section such as Type No. OPB806 Photo Detector manufactured by TRW. Switch means 18 is mounted so that inertia rod 20 is movable between the light energy emitting and light energy sensing sections of switch means 18. Activation of optical switch means 18 by movement of slot 58 therethrough and the resultant signal are directed to kinetic energy display assembly 62, seen in FIG. 7, through wiring harness 64.

Display assembly 62 is essentially a small computer which calculates the impact energy of hammer 10 upon the primary pressure boundary. This information is derived in the following manner. The relative velocity between head 12 and inertia rod 20 may be determined by the use of the formula V=distance divided by time, where V equals velocity, distance equals slot width and time equals time for slot 58 to pass through optical switch 18. The impact energy with which hammer 10 strikes the primary pressure boundary is determined from the following equation:

$$E = \tfrac{1}{2} M (k^*d/t)^2$$

Where $E$ = impact energy
$M$ = mass of hammer 10
$k$ = f(coefficient of restitution response time errors)
$t$ = time for slot 58 to pass through optical switch 18
$d$ = slot width Note $k^*d$ is experimentally determined by dropping the known mass a known distance (the impact energy which is known from common calculations), reading the results on meter 66, and making any adjustments necessary to the $k^*d$ term in the computer to display the correct impact energy on meter 66. Because this is a non-linear response, two drop distances at the range extremes are used to derive the software coefficients in calibrating the computer. Also, minor adjustments in the value of d (slot width) are possible by use of a potentiometer in the computer. As the actual slot width 'd' is a dimension controlled in fabrication, the computer measures the time 't' that is taken for slot 58 to pass through optical switch 18 when a hammer strike is made. A potentiometer, such as trimmer pot R14, R15, or R16 may be used to adjust the optical trigger set point of optical switch 18, which effectively adjusts the value of the width "d" of slot 58. This adjustment is required to trim the value of slot width "d" to match the computer constant K times d such that the measured impact energies are correct.

Figure 3:
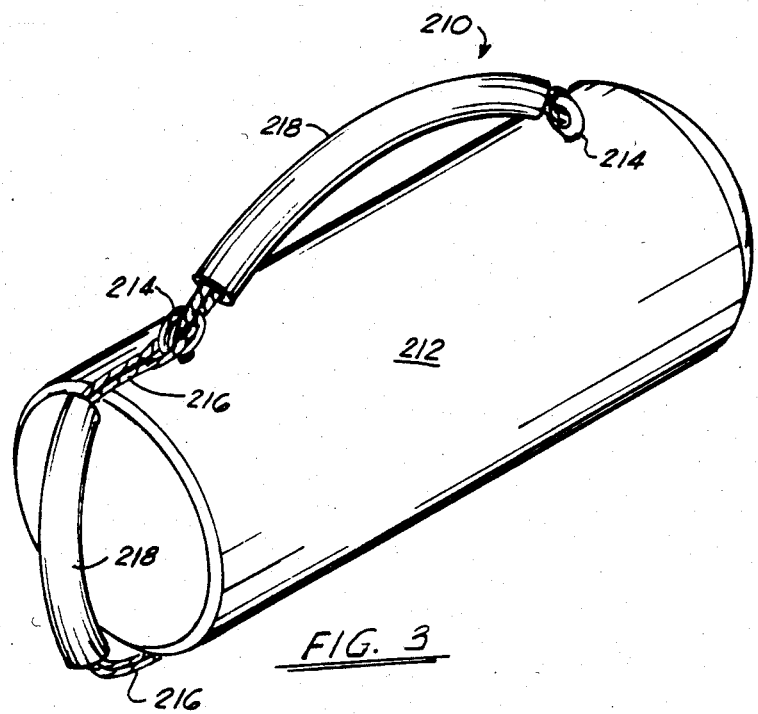
FIG. 3 is a perspective view of a third size hammer of the invention.

As previously stated, three different weight hammers are utilized. For ease of description, the internal structure of the 0.25 lb. hammer has been described. The basic operating structure and principles of each are the same. It can be seen in FIGS. 2 and 3 illustrating 2 lb. hammer 110 and 30 lb. hammer 210 that the major structural difference is that of head mass. Also, 30 lb. hammer 210 is provided with a different handle arrangement for ease of operation. Head 212 is provided with screw eyes 214 at the top of the front and rear ends and at the bottom of the rear end. Any suitable material such as nylon rope 216 is attached to screw eyes 214 and encased by a nonabrasive material such as rubber hose 218 for handling ease.

Slot 58 in inertia rod 20 is also of a slightly different width for each weight hammer. The length of slot 58 in each different weight hammer is preferably 0.10 inch. The width W of slot 58 is preferably 0.080 inch for the 0.25 lb. hammer, 0.060 inch for the 2 lb. hammer, and 0.040 inch for the 30 lb. hammer. A manufacturing tolerance of plus or minus 0.003 inch is acceptable. With regard to material, the majority of hammer 10 and its components such as the head, inertia rod, guide bushing, stop rings, and screws are formed from stainless steel.

In operation, guide bushing 22 is used to adjust the position of inertia rod 20 so that the leading edge of slot 58 is 0.010 to 0.025 inch away from the rear edge of optical switch 18. Also, a sufficient number of stop rings 44 and 48 are used so that the rear end of inertia rod 20 is flush (0.000–0.020 inch) with second end 26 of head 12 when inertia rod 20 is fully inserted in longitudinal bore 42 in its second inserted position against spring 46. The operator then drops hammer 10 (a known mass)

twice at specified distance range extremes and the reading on meter 66 is compared to standard calculations for determining impact energy. Any adjustments necessary to calibrate display assembly 62 are then made through trimmer pots R14, R15, and R16. The operator then makes hammer strikes the required distance away from LPMS sensors on the primary pressure boundary and voice relays via a wire impact energy readings of the strikes to the operator of the LPMS for correlation with the LPMS sensor response. Loose parts data is characterized by both amplitude response, to estimate the impact energy of the loose part, and time delay triangulation, to locate the impact point of origin. Although time delay data does not require a calibrated impact hammer, ordinarily the time delay and amplitude responses are done simultaneously. As stated above, the hammer operator must strike the piping or vessel structure at a known location. The time delay triangulations are then recorded at the loose parts monitor cabinet. Hammer 10 thus provides a tool which can be used to strike a surface of any orientation and eliminates guesswork and inaccuracies often encountered in determining impact energy.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed is:

1. A calibration impact hammer, comprising:
   (a) a head with first and second ends having a longitudinal bore extending from said second end toward said first end, said longitudinal bore being threaded at said second end;
   (b) an inertia rod slidably received within said longitudinal bore and movable between a first normal retracted position and a second inserted position;
   (c) means in said longitudinal bore for biasing said inertia rod toward said first normal position;
   (d) optical switch means mounted on said second end of said head;
   (e) means on said inertia rod for activating said optical switch means upon movement of said inertia rod between said first and second positions;
   (f) means threadably engaged in said longitudinal bore for slidably receiving and adjusting the position of said inertia rod relative to said optical switch means; and
   (g) display means connected to said optical switch means for receiving signals therefrom and calculating and displaying the impact energy of said hammer upon striking a surface.

2. The hammer of claim 1, wherein said inertia rod moves from said first to said second position in response to striking said hammer against a surface.

3. The hammer of claim 1 wherein said biasing means comprises a spring.

4. The hammer of claim 1 wherein said means for activating said optical switch means comprises said inertia rod having a slot therethrough located such that movement of said rod between said first and second positions causes movement of said slot through said optical switch means.

5. The hammer of claim 1, wherein said adjusting means comprises a guide bushing.

6. The hammer of claim 1, further comprising a handle attached to said head.

7. A calibration impact hammer, comprising:
   (a) a head with first and second ends having a longitudinal bore extending from said second end toward said first end, said longitudinal bore being threaded at said second end;
   (b) an inertia rod slidably received within said longitudinal bore and movable between a first normal retracted position and a second inserted position in response to striking said hammer against a surface;
   (c) spring means in said longitudinal bore for biasing said inertia rod toward said first normal position;
   (d) optical switch means mounted on said second end of said head;
   (e) means on said inertia rod for activating said optical switch means upon movement of said inertia rod between said first and second positions;
   (f) means threadably engaged in said threaded bore portion for slidably receiving and adjusting the position of said inertia rod relative to said optical switch means; and
   (g) display means connected to said optical switch means for receiving signals therefrom and calculating and displaying the impact energy of said hammer upon striking the surface.

8. The hammer of claim 7, wherein said means for activating said optical switch means comprises said inertia rod having a slot therethrough located such that movement of said rod between said first and second positions causes movement of said slot through said optical switch means.

9. The hammer of claim 7, wherein said adjusting means comprises a guide bushing.

10. The hammer of claim 7, further comprising a handle attached to said head.

11. A calibration impact hammer, comprising:
    (a) a head with first and second ends having a longitudinal bore extending from said second end toward said first end, said longitudinal bore being threaded at said second end;
    (b) an inertia rod slidably received within said longitudinal bore and movable between a first normal retracted position and a second inserted position;
    (c) a spring housed in said longitudinal bore for biasing said inertia rod toward said first normal position;
    (d) an optical switch mounted at said second end of said head adjacent said inertia rod;
    (e) said inertia rod having a slot therethrough whereby movement of said rod between said first and second positions causes movement of said slot through said optical switch and activation of said switch;
    (f) means threadably engaged in said threaded bore portion for adjusting the position of said slot relative to said optical switch; and
    (g) display means connected to said optical switch for receiving signals therefrom and calculating and displaying the impact energy of said hammer upon striking a surface.

12. the hammer of claim 11, wherein said inertia rod moves from said first normal position to said second position in response to striking said hammer against a surface.

13. The hammer of claim 11, wherein said adjusting means comprises a guide bushing.

14. the hammer of claim 11, further comprising a handle attached to said head.

* * * * *